United States Patent
Hemphill

(10) Patent No.: US 11,026,757 B2
(45) Date of Patent: Jun. 8, 2021

(54) SURGICAL CANNULAS, AND RELATED SYSTEMS AND METHODS

(71) Applicant: Intuitive Surgical Operations, Inc., Sunnyvale, CA (US)

(72) Inventor: Jason Hemphill, Los Gatos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 118 days.

(21) Appl. No.: 15/624,148

(22) Filed: Jun. 15, 2017

(65) Prior Publication Data

US 2018/0021098 A1 Jan. 25, 2018

Related U.S. Application Data

(60) Provisional application No. 62/364,563, filed on Jul. 20, 2016.

(51) Int. Cl.
| | |
|---|---|
| *A61B 34/35* | (2016.01) |
| *A61B 18/18* | (2006.01) |
| *A61B 34/00* | (2016.01) |
| *A61B 17/34* | (2006.01) |
| *A61B 18/14* | (2006.01) |
| *A61B 34/30* | (2016.01) |
| *A61B 90/98* | (2016.01) |

(Continued)

(52) U.S. Cl.
CPC .......... *A61B 34/35* (2016.02); *A61B 17/3421* (2013.01); *A61B 18/14* (2013.01); *A61B 18/18* (2013.01); *A61B 34/25* (2016.02); *A61B 34/30* (2016.02); *A61B 34/70* (2016.02); *A61B 18/16* (2013.01); *A61B 90/98* (2016.02); *A61B 2017/00477* (2013.01); *A61B 2017/00876* (2013.01)

(58) Field of Classification Search
CPC ......... A61B 34/35; A61B 34/25; A61B 34/30; A61B 34/70; A61B 17/3421; A61B 18/14; A61B 18/18; A61B 90/98; A61B 18/16; A61B 2017/00477; A61B 2017/00876
USPC ............................................................ 606/1
See application file for complete search history.

(56) References Cited

U.S. PATENT DOCUMENTS

| | | | |
|---|---|---|---|
| 6,331,181 B1 * | 12/2001 | Tierney ................. | G16H 40/63 606/130 |
| 8,852,208 B2 | 10/2014 | Gomez et al. | |

(Continued)

FOREIGN PATENT DOCUMENTS

| | | |
|---|---|---|
| WO | WO-2013056121 A2 | 4/2013 |
| WO | WO-2015142812 A1 | 9/2015 |
| WO | WO-2015142814 A1 | 9/2015 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Erin M Piateski
(74) *Attorney, Agent, or Firm* — Jones Robb, PLLC

(57) ABSTRACT

A surgical cannula includes an electrically conductive portion, an electrical connector interface configured to removably engage with an electrical connector electrically coupled to a patient return electrode, and an electrical connector sensing device configured to sense whether the electrical connector interface is engaged or disengaged with the electrical connector. Surgical systems include surgical cannulas. Methods relate to surgical cannulas.

19 Claims, 8 Drawing Sheets

(51) Int. Cl.
    *A61B 17/00*      (2006.01)
    *A61B 18/16*      (2006.01)

(56)            References Cited

U.S. PATENT DOCUMENTS

| 2011/0087212 | A1* | 4/2011  | Aldridge    | H01L 41/042 |
|              |     |         |             | 606/34      |
| 2012/0078245 | A1* | 3/2012  | Morrissette | A61B 18/14  |
|              |     |         |             | 606/34      |
| 2013/0325031 | A1  | 12/2013 | Schena et al. | |
| 2013/0325033 | A1  | 12/2013 | Schena et al. | |
| 2013/0331858 | A1* | 12/2013 | Devengenzo  | A61B 34/30  |
|              |     |         |             | 606/130     |
| 2015/0150546 | A1* | 6/2015  | Goldschmidt | A61B 90/98  |
|              |     |         |             | 606/1       |
| 2016/0074093 | A1* | 3/2016  | Shimizu     | A61B 18/1206 |
|              |     |         |             | 606/35      |
| 2016/0270780 | A1* | 9/2016  | Hall        | A61B 34/74  |

* cited by examiner

SURGICAL CANNULAS, AND RELATED SYSTEMS AND METHODS

CROSS-REFERENCE TO RELATED APPLICATIONS

This application claims priority to U.S. Provisional Application No. 62/364,563, filed Jul. 20, 2016, which is incorporated by reference herein in its entirety.

TECHNICAL FIELD

Aspects of the present disclosure relate to surgical cannulas having electrical grounding, and related systems and methods.

INTRODUCTION

Remotely-controlled surgical instruments, which can include teleoperated surgical instruments (e.g., surgical instruments operated at least in part with computer assistance, such as instruments operated with robotic technology) as well as manually operated (e.g., laparoscopic, thorascopic) surgical instruments, are often used in minimally invasive medical procedures. During such procedures, a surgical instrument, which may extend through a cannula inserted into a patient's body, can be remotely manipulated to perform a procedure at a surgical site. For example, in a teleoperated surgical system, cannulas and surgical instruments can be mounted at manipulator arms of a patient side cart and be remotely manipulated via teleoperation at a surgeon console.

Teleoperated surgical instruments may include parts made of metal or other electrically conductive materials. Conductive materials can become electrically charged in a surgical environment. When such an electrical charge discharges, the discharge may occur in undesirable and/or unanticipated locations as the charge seeks a path to a lower electric potential. In addition, a discharge can potentially damage the instrument, particularly if the instrument includes electrical components.

Accordingly, electrically conductive portions of a surgical cannula are often electrically coupled to the patient's body to dissipate charge from surgical instruments and prevent buildup of electrical charge. Such electrical coupling may be achieved by connecting an electrical conductor between the electrically conductive portions of the surgical cannula and the patient's body, and the patient may be electrically coupled to a reference electrical potential associated with an electrosurgical energy generator unit that supplies energy to a surgical instrument that is inserted through the cannula. The electrical coupling between the conductive portions of the cannula and the patient's body can be achieved by connecting a conductor (e.g., a cable, wire, etc.) between an electrode in contact with the patient's body and the conductive portions of the cannula.

It is desirable to improve upon cannula electrical grounding to facilitate surgical procedures using electrical energy.

SUMMARY

Exemplary embodiments of the present disclosure may solve one or more problems and/or may demonstrate one or more desirable features, which will become apparent from the description that follows.

In accordance with various exemplary embodiments, a surgical cannula includes an electrically conductive portion, an electrical connector interface configured to removably engage with an electrical connector electrically coupled to a patient return electrode, and an electrical connector sensing device configured to sense whether the electrical connector interface is engaged or disengaged with the electrical connector.

In accordance with various exemplary embodiments, a surgical system includes a surgical manipulator and a cannula. The cannula includes an attachment portion configured for attachment to the surgical manipulator, an electrical connector interface configured to removably engage with an electrical connector electrically coupled with a patient return electrode, and an electrical connector sensing device configured to provide information to a controller of the surgical system regarding an engaged or disengaged state of the electrical connector with the electrical connector interface.

In accordance with various exemplary embodiments, a method includes positioning an electrode in conductive contact with an electrically conductive body and engaging an electrical connector operatively coupled to the electrode to an electrical connector interface of a surgical cannula. Engaging the electrical connector with the electrical connector interface electrically couples the electrical connector and the electrical connector interface of the surgical cannula. The method includes changing a state of an electrical connector sensing device responsive to the engaging of the electrical connector and the electrical connector interface of the surgical cannula.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

Both the foregoing general description and the following detailed description are exemplary and explanatory only and are not restrictive of the claims; rather, the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
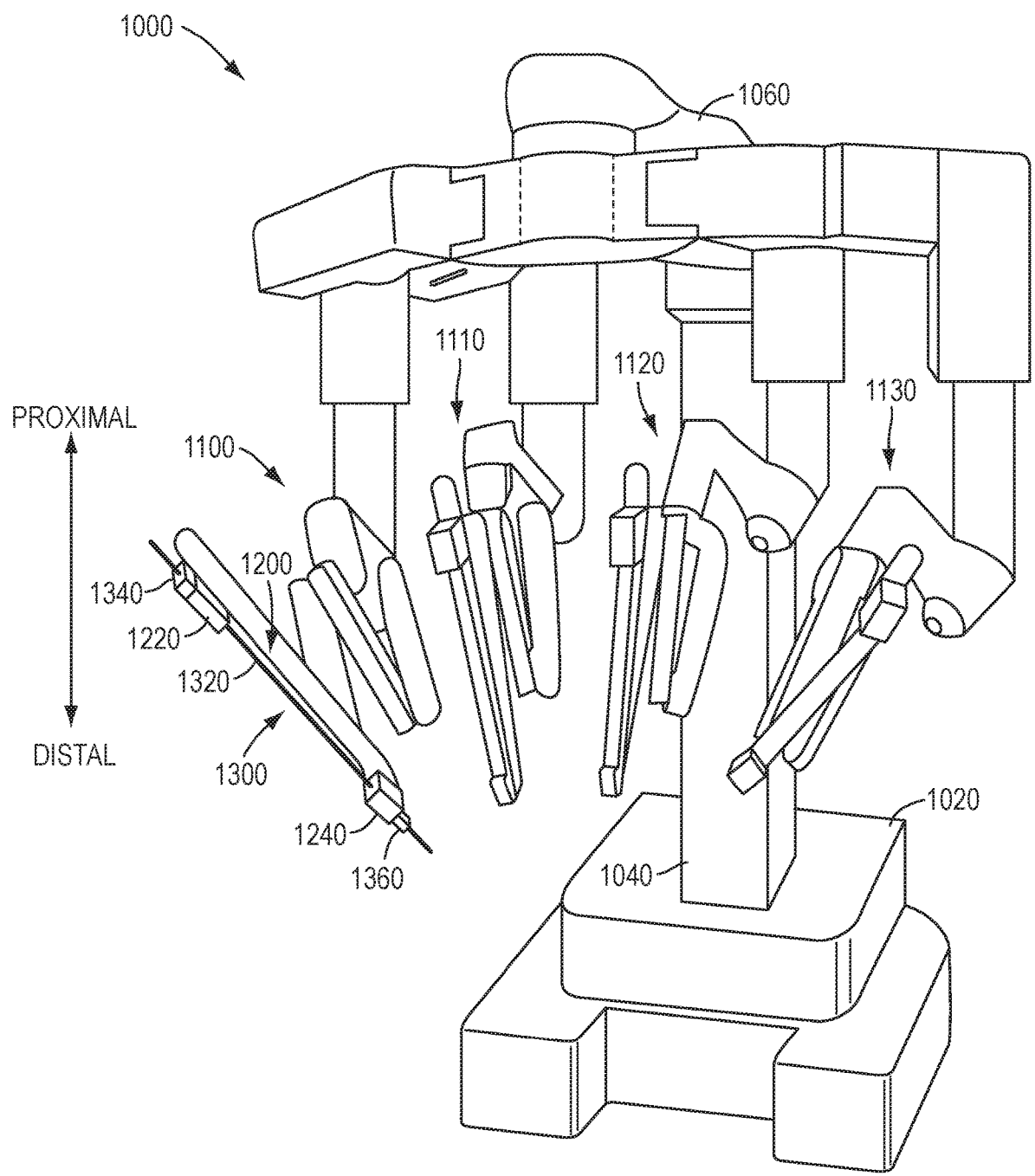
FIG. 1 is a front view of an exemplary embodiment of a patient side cart of a teleoperated, computer-assisted surgical system.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "top", "bottom", "lower", "upper", "below", "above", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

Various exemplary embodiments of the present disclosure include surgical cannulas configured to provide information to a surgical system regarding a connected state or disconnected state of an electrical conductor, such as an electrode and an associated cable and connector, configured to form a conductive path between an electrically conductive portion of the surgical cannula and a patient's body. The electrode in contact with the patient may be characterized as a "return electrode"; for example, while the electrode may in one sense be considered to "ground" the cannula to the patient, the voltage potential of the patient is not necessarily equal to earth ground. In accordance with an exemplary embodiment of the disclosure, the connected or disconnected state of the return electrode connector is indicated by the position and/or polarity of one or more magnets disposed within the body of the cannula. For example, one or more sensors configured to recognize the presence and/or polarity of a magnet may be included in a component, such as a manipulator arm, of a remotely controlled surgical system. In some embodiments, the connected or disconnected state of the return electrode connector may be indicated by a radio frequency identification (RFID) device of the cannula, an electromagnetic or optical proximity sensor, or by other techniques.

Exemplary embodiments described herein may be used, for example, with a teleoperated, computer-assisted surgical system (sometimes referred to as robotic surgical systems) such as that described in, for example, U.S. Patent App. Pub. No. US 2013/0325033 A1, entitled "Multi-Port Surgical Robotic System Architecture" and published on Dec. 5, 2013, U.S. Patent App. Pub. No. US 2013/0325031 A1, entitled "Redundant Axis and Degree of Freedom for Hardware-Constrained Remote Center Robotic Manipulator" and published on Dec. 5, 2013, and U.S. Pat. No. 8,852,208, entitled "Surgical System Instrument Mounting" and published on Oct. 7, 2014, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although various exemplary embodiments described herein are discussed with regard to surgical instruments used with a patient side cart of a teleoperated surgical system, the present disclosure is not limited to use with surgical instruments for a teleoperated surgical system. For example, various exemplary embodiments of surgical cannulas described herein can optionally be used in conjunction with hand-held, manual surgical instruments.

Referring now to FIG. 1, an exemplary embodiment of a patient side cart 1000 of a teleoperated, computer-assisted surgical system is shown. A teleoperated surgical system may further include a surgeon console (not shown) for receiving input from a user to control instruments mounted at patient side cart 1000. According to an exemplary embodiment, patient side cart 1000 includes a base 1020 and a main column 1040. The patient side cart 1000 also includes a plurality of teleoperated manipulator arms 1100, 1110, 1120, 1130 (sometimes referred to as patient side manipulators), which are each connected to the main column 1040 as depicted in the exemplary embodiment of FIG. 1. Manipulator arms 1100, 1110, 1120, 1130 may each include an instrument mount portion 1200 to which an instrument 1300 may be mounted. Portions of the manipulator arms 1100, 1110, 1120, 1130 may be manipulated during a surgical procedure according to commands provided by a user at the surgeon console. In an exemplary embodiment, signal(s) or input(s) transmitted from a surgeon console are transmitted to the control/vision cart, which interprets the input(s) and generate command(s) or output(s) to be transmitted to the patient side cart 1000 to cause manipulation of an instrument 1300 (only one such instrument being mounted in FIG. 1) and/or portions of manipulator arm 1100 to which the instrument 1300 is coupled at the patient side cart 1000.

Instrument mount portion 1200 may comprise an actuation interface assembly 1220 and a cannula mount 1240. A shaft 1320 of instrument 1300 extends through cannula mount 1240 and mounted cannula, and on to a remote site during a surgical procedure. A force transmission mechanism 1340 at a proximal end of instrument 1300 is mechanically coupled with the actuation interface assembly 1220, according to an exemplary embodiment. Persons skilled in the art are familiar with surgical instrument force transmission mechanisms, which receive a mechanical input force from a source (e.g., an electric motor on a manipulator arm supporting the instrument) and convert and/or redirect the received force to an output force to drive a component (e.g., a wrist, an end effector, etc.) at a relatively distal end portion of the instrument. Cannula mount 1240 may be configured to hold a cannula 1360 through which shaft 1320 of instrument 1300 may extend to a surgery site during a surgical procedure. Actuation interface assembly 1220 may contain a variety of drive and other mechanisms that are controlled to respond to input commands at the surgeon console and transmit forces to the force transmission mechanism 1340 to actuate instrument 1300, as those skilled in the art are familiar with.

Figure 2:
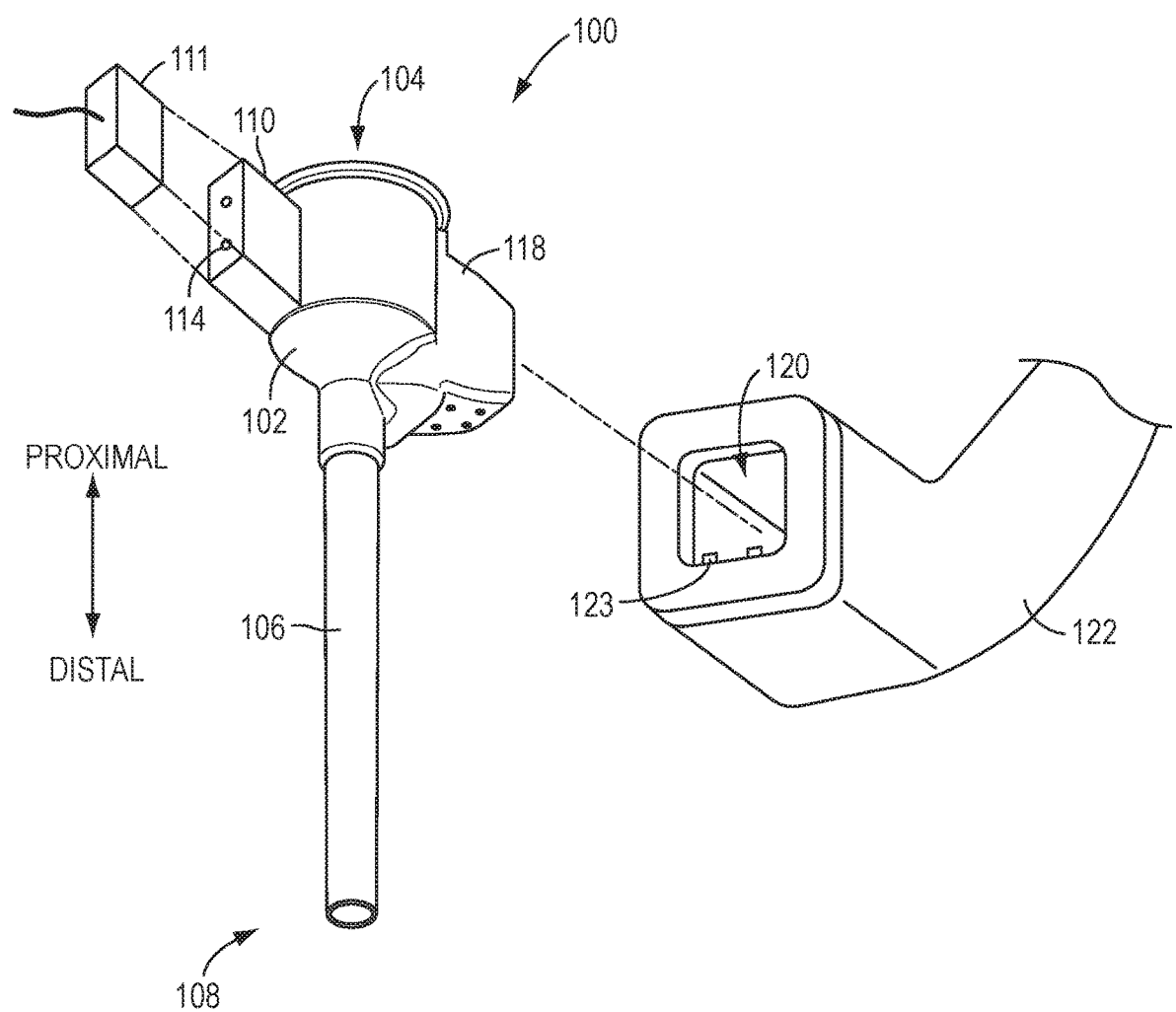
FIG. 2 is a perspective view of a cannula and a portion of a surgical instrument manipulator according to an exemplary embodiment.

Referring now to FIG. 2, a cannula 100 according to an embodiment of the disclosure is shown. The cannula 100 includes a bowl portion 102 forming a proximal end 104 of the cannula and a tube 106 extending from the bowl portion 102 to a distal end 108 of the cannula 100. A portion of the cannula 100 may be inserted at least partially through an opening in a patient's body to a surgical site. For example, the distal end 108 of the cannula 100 may be inserted through an opening, such as an incision or natural orifice, with or without a surgical port, to the surgical site. A surgical instrument (e.g., surgical instrument 1300 shown in FIG. 1) may be inserted into the proximal end 104 of the cannula 100 and extended through the bowl portion 102, the tube 106, and out through the distal end 108 of the cannula 100 to a surgical site.

Figure 3:
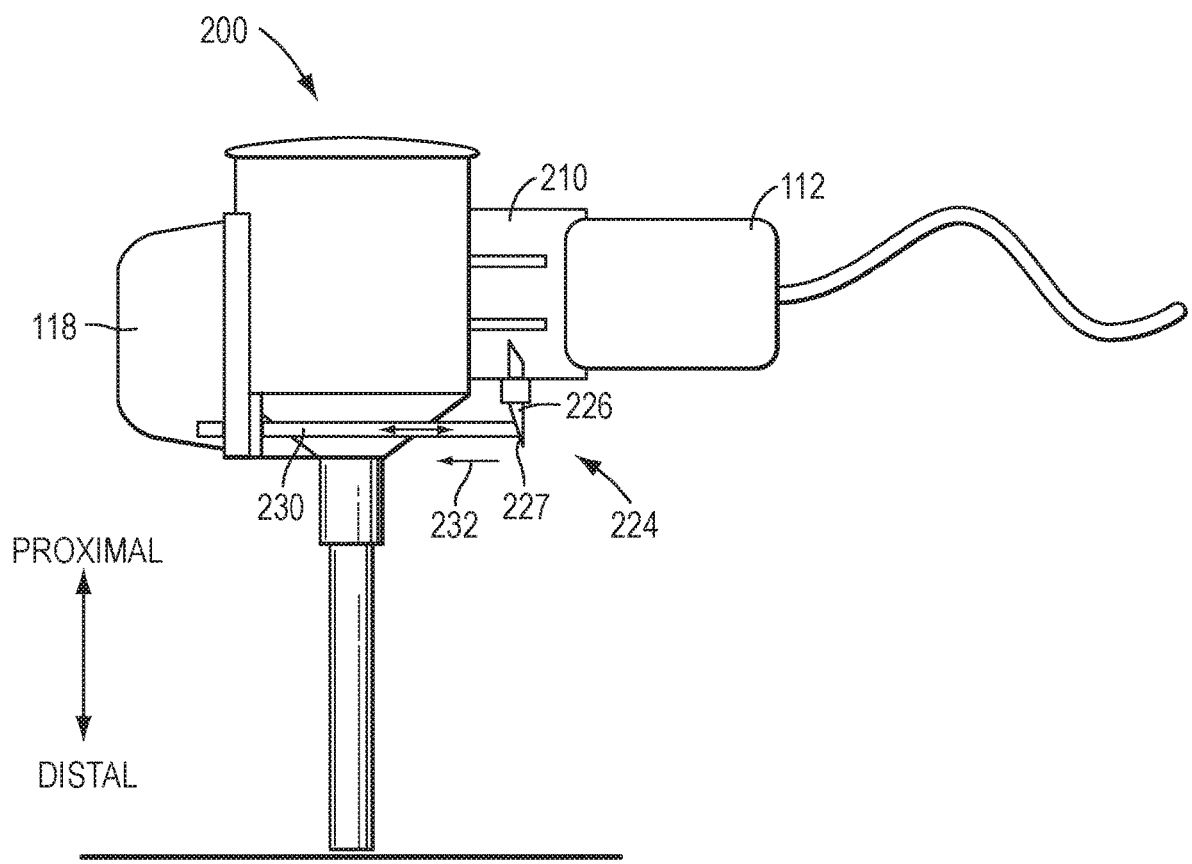
FIG. 3 is a side diagrammatic view of a cannula and a patient return electrode connector according to an exemplary embodiment.

The cannula 100 may include a return electrode connector interface 110 configured to accept a return electrode connector 112 (FIG. 3). The return electrode connector interface 110 may include one or more electrical contacts 114 configured to conductively couple with mating electrical contacts (not shown) of the return electrode connector 112. The return electrode connector interface 110 may also be characterized as a complementary electrical connector. The electrical contacts 114 may form a portion of a conductive path between electrically conductive portions of the cannula 100 and a body of a patient through a conductor (e.g., wire) 116 (FIG. 3) connected to an electrode conductively coupled to a patient's body (e.g., electrode 650 shown in FIG. 9).

In exemplary embodiments, the interface 110 may be configured as a female connector portion (e.g., a receptacle) and the return electrode connector 112 may be configured as a male connector portion (e.g., a plug). Alternatively, the interface may be configured as a male connector portion (e.g., a plug) and the return electrode connector 112 may be configured as a female connector portion (e.g., a receptacle).

The cannula 100 may include an attachment portion 118 configured to attach the cannula 100 to a component (e.g., patient side manipulator or arm) of a surgical system, such as that described in detail in Intl Pub. No. WO2015/0142812, filed Mar. 17, 2015 and entitled "Surgical Cannulas and Related Systems and Methods of Identifying Surgical Cannulas," which is incorporated by reference herein in its entirety. For example, as shown in FIG. 2, the attachment portion 118 of the cannula 100 may be configured to be inserted within a receptacle 120 of a manipulator arm 122 (e.g., manipulator arm 1100 (FIG. 1)) (also called "manipulator 122") of a patient side cart. When inserted within the manipulator arm receptacle 120, the attachment portion 118 may be electrically insulated from the manipulator arm 122.

The cannula 100 may include a sensing system (e.g., sensing device, sensing component, etc.) configured to provide information relating to the connected or disconnected status of the return electrode connector 111 with the return electrode connector interface 110 of the cannula 100. The provided information is transmitted through the manipulator arm 122 to the teleoperated surgical system, and the teleoperated surgical system indicates the connected or disconnected status of the return electrode connector 111 to an operator (e.g., nurse, surgeon, technician, etc.) with a visual indicator such as a warning light or a message on a display screen, an audible indicator such as an alarm, or another indicator. Such an indicator may be included in a display portion (not shown) of the teleoperated surgical system. Additionally or alternatively, the teleoperated surgical system may include a lockout system configured to disable a function of a surgical instrument when the return electrode connector 111 is determined to be in a disconnected state from the interface 110. For example, the surgical system may be configured to prevent application of electrical power to a surgical instrument (e.g., surgical instrument 646 shown in FIG. 9), such as an electrocautery tool, when the return electrode connector 111 is not connected at the return electrode connector interface 110 of the cannula 100.

The sensing system can include one or more of mechanical devices, optical devices, electrical devices, magnetic devices and/or other sensing devices. As a non-limiting example, the sensing system may include a component of the cannula 100 configured to be recognized by a sensor in the manipulator arm 122 of the teleoperated surgical system. For example, the sensing component of the cannula 100 may be configured to be recognized by one or more of a proximity sensor, such as a photoelectric or electromagnetic sensor, a radio-frequency identification (RFID) sensor, a Hall-effect sensor, etc. of the manipulator arm 122. In some exemplary embodiments, the sensing component may be configured to change from a first state to a second state when the return electrode connector 112 is in a connected state with the return electrode connector receptacle comprising the return electrode connector interface 110 of the cannula 100.

In various exemplary embodiments, the first state and the second state may include, for example, a position, orientation, or other physical configuration of the sensing component, an electrical or magnetic state of the component, etc. For example, the first state and the second state may refer to physical positions and/or orientations of a magnet sensed by, e.g., a hall-effect sensor or other magnetic sensor, a shutter or other component sensed by a proximity sensor, etc. In some exemplary embodiments, the first state and the second state may refer to energized and non-energized states of a passive RFID tag, transmitting and non-transmitting states of a battery-assisted passive RFID tag, etc. In an exemplary embodiment, changing the state of the electrical connector sensing device includes changing radio-frequency electromagnetic waves (e.g., those being emitted by an RFID tag) being sensed by an electrical connector sensing device (e.g., an RFID sensor).

In various exemplary embodiments, the return electrode connector interface 110 is positioned laterally opposite to the attachment portion 118 of the cannula 100. With reference now to FIG. 3, cannula 200 has a mechanical device 224 located between the attachment portion 118 of the cannula 200 and a return electrode connector interface 210 (also called "return electrode connector receptacle 210" in various embodiments). The mechanical device 224 is configured to alter in position and/or configuration when the return electrode connector 112 is engaged (e.g., mated) with the return electrode connector interface 210, such as being inserted within a receptacle of the return electrode connector interface 210. In some exemplary embodiments, the position and/or orientation of a component within or near the attachment portion 118 of the cannula may be altered by the mechanical device 224 responsive to the act of engaging or disengaging the return electrode connector 112 with the return electrode connector 112.

For example, in the exemplary embodiment of FIG. 3, the cannula 200 includes a pushrod 230 extending laterally across a portion of the cannula 200 from the return electrode connector interface 210 to the attachment portion 118. The pushrod 230 may be in contact with a plunger 226 that is configured to extend at least partially into the return electrode connector receptacle 210 when the return electrode connector is not located within the return electrode connector receptacle 210. Insertion of the return electrode connector 112 within the return electrode connector receptacle 210 may cause the return electrode connector 112 to push against the plunger 226, forcing the plunger 226 to move downward (i.e., in a direction away from the return electrode connector 112 and generally parallel to a longitudinal axis of the cannula 200). Interaction between the pushrod 230 and the plunger 226 may convert the longitudinal motion of the plunger 226 to lateral movement in the pushrod 230, forcing the pushrod 230 to move in direction 232. For example, in the exemplary embodiment of FIG. 3, complementary inclined planes 227 of the pushrod 230 and the plunger 226 convert the longitudinal motion of the plunger 226 to lateral movement of the pushrod 230. Thus, insertion of the return electrode connector 112 within the return electrode connector receptacle 210 causes the pushrod 230 to move from a position representing a disconnected state of the return electrode connector 112, to another position along direction 232 representing a connected state of the return electrode connector 112. Movement of the pushrod 230 in turn changes the position and/or orientation of a sensing device disposed within the attachment portion 118, as discussed in greater detail in connection with the exemplary embodiments of FIGS. 3 and 4 below.

Other structures and configurations may be used to cause a change in state (e.g., position, orientation, etc.) of a component of the sensing system. For example, in other exemplary embodiments, the pushrod 230 and the plunger 226 are a single rigid part configured to translate laterally as a unit in response to the return electrode connector being engaged with the return electrode interface 210. In some exemplary embodiments, the pushrod 230 may be replaced by a pivoting lever, or by any other mechanism configured to transfer movement between the return electrode connector 112 and an sensing device within the attachment portion 118. In some embodiments, the pushrod 230, or other mechanism of the sensing system, is biased, e.g., by a spring or other biasing element, to ensure that the sensing system returns to a position representing the disconnected state of the return electrode connector 112 when the return electrode connector 112 is removed from the return electrode connector receptacle 210.

Figure 4:
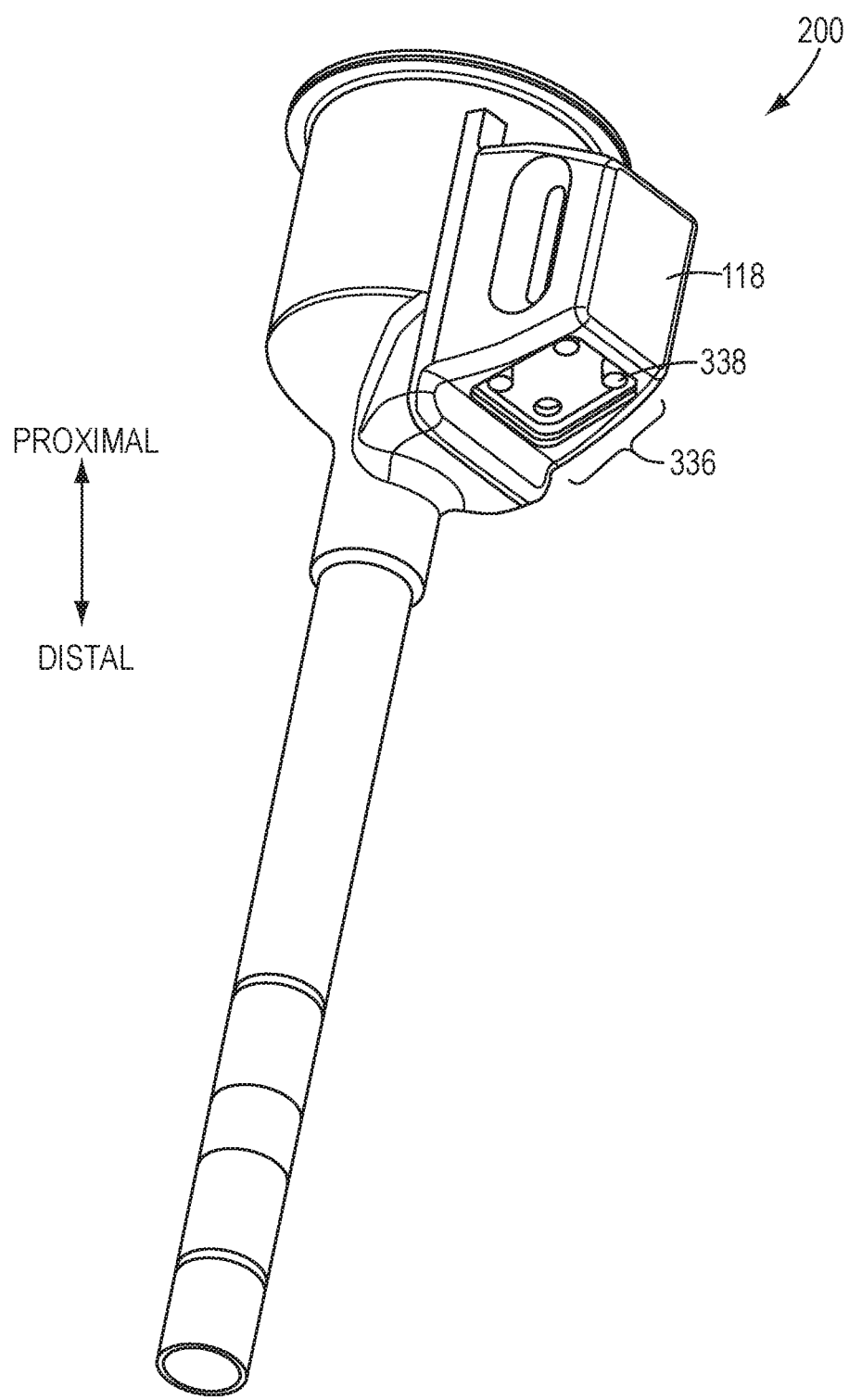
FIG. 4 is a perspective view of a cannula according to an exemplary embodiment.

Referring now to FIG. 4, another view of the cannula 200 of FIG. 3 is shown. As seen in FIG. 4, the attachment portion 118 of the surgical cannula 200 may include an array of magnets 336 (e.g., a 2×2 array being depicted) (also called "array 336"). The array of magnets 336 and related portions of the surgical cannula 200 may be substantially as described at least in Intl Pub. No. WO 2015/0142812, as incorporated by reference above. As described therein, the array of magnets 336 is configured to interact with sensors (e.g., Hall-effect sensors) disposed within a manipulator (e.g., manipulator 122 (FIG. 2)) to identify various aspects or parameters of the cannula 100. For example, as discussed in WO 2015/0142812, the presence, absence, and/or polarity of each magnet of the array of magnets 336 can be associated with a particular aspect of the cannula 200 such as bowl diameter, length, shape of tube, number of uses, etc. Sensors within the manipulator 122 transmit information regarding the presence and/or polarity of each magnet of the array 336 to the surgical system, where information regarding the particular combination of magnets and polarity is utilized by a processor or controller and memory to identify the configuration and/or state of the cannula 200.

In addition, in accordance with exemplary embodiments of the disclosure, the information provided to the surgical system by the array of magnets 336 include the connected or disconnected state of the return electrode connector 112. For example, the combination of presence and/or polarity of the magnets of the array 336 can be used to identify the particular design of the cannula 200 (e.g., bowl diameter, tube length, shape of tube, etc.) and the position and/or polarity of one or more magnets of the array 336 also indicates whether the return electrode connector 112 is in a connected state with the cannula 200.

In an exemplary embodiment, a magnet 338 of the array 336 is mechanically coupled with the pushrod 230 (FIG. 3), such that movement of the pushrod 230 (e.g., as the return electrode connector 112 is inserted within or removed from the return electrode connector receptacle 210 (FIG. 3)) causes a corresponding movement of the magnet 338. For example, the magnet 338 may be mechanically coupled directly with the pushrod 230 or through a linkage, a rack and pinion gear, etc., or any other suitable mechanical device. Movement of the pushrod 230 from a first position associated with the absence of the return electrode connector 112 from the return electrode connector receptacle 210 to a second position associated with the presence of the return electrode connector 112 within the return electrode connector receptacle comprising the return electrode connector interface 110 thereby moves the magnet 338 from a first position, configuration, and/or orientation to a second position, configuration, and/or orientation in a manner recognized by a sensor within the manipulator 122 (FIG. 2).

In an exemplary embodiment, movement of the magnet 338 comprises translational movement from a first position within the attachment portion 118 to a second position within the attachment portion 118. In the first position, the magnet 338 is positioned proximate (e.g., within a sensing range of) a sensor, such as a Hall-effect sensor 123 (FIG. 2), within the receptacle 120 (FIG. 2) of the manipulator arm 122 (FIG. 2) when the attachment portion 118 is disposed within the receptacle 120. In the second position, the magnet 338 is positioned out of the sensing range of the sensor 123 when the attachment portion 118 is disposed within the receptacle 120. In other words, inserting the return electrode connector 112 within the return electrode connector receptacle 210 (FIG. 3) moves the magnet 338 from a first position in which the magnet 338 is within a sensing range of the sensor 123 in the manipulator 122, to a second position in which the magnet 336 is not within the sensing range of the sensor 123 in the manipulator 122. The presence or absence of the magnet 338 from the sensing range of the sensor 123 indicates to the surgical system the connected or disconnected status of the return electrode connector 112.

Figure 5:
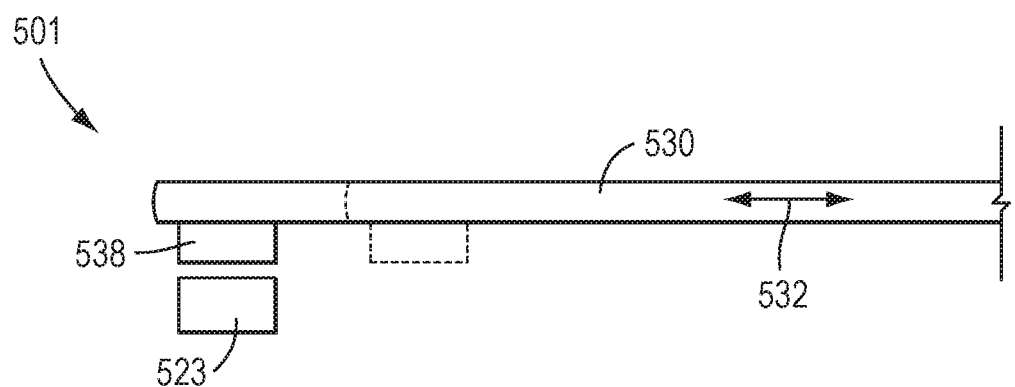
FIG. 5 is a schematic view of a portion of a cannula and a portion of a surgical instrument manipulator according to an exemplary embodiment.

For example, with reference now to FIG. 5, a schematic view of an exemplary embodiment of a portion of a return electrode sensing device 501 is shown. In the embodiment of FIG. 5, a pushrod 530 supports a magnet 538, which may, in some exemplary embodiments, form a portion of an array of magnets (e.g., array 336 shown in FIG. 4). The pushrod 530 is configured to move along direction 532 as a return electrode connector (e.g., the return electrode connector 111 in FIG. 2) is engaged with, or removed from, a return electrode connector interface (e.g., the return electrode connector interface 110 in FIG. 3). As shown in FIG. 5, the magnet 538 may be disposed proximate (e.g., within a sensing range of) a sensor 523 (similar to, e.g., sensor 123 discussed in connection with FIG. 2) when the pushrod 530 is in a position associated with the return electrode connector being engaged with the return electrode connector interface, as shown in solid lines in FIG. 5. When the return electrode connector is disengaged from the return electrode connector interface, the pushrod 530 and magnet 538 are positioned as shown in the dashed lines in FIG. 5, and the magnet 538 is positioned outside of a sensing range of the sensor 523. Information regarding the position of the magnet 538 within, or outside of, the sensing range of the sensor 523 is processed by the surgical system to provide, e.g., a warning indication at a user interface (not shown) of the surgical system, a lockout condition, etc.

Additionally or alternatively, movement of the magnet 338 may comprise movement that changes the pole of the magnet 338 presented to the sensor 123 of the receptacle 120 of the manipulator 122 (FIG. 2). For example, in a first rotational position, one of the north pole and the south pole of the magnet is proximate the sensor 123 within the receptacle 120 of the manipulator 122. Movement of the pushrod 230 causes the magnet 336 to rotate until the other of the north pole and south pole is proximate the sensor 123. Accordingly, the polarity of the magnet 338 presented to the sensor 123 may be used to determine the connected or disconnected status of the return electrode connector 112.

Figure 6:
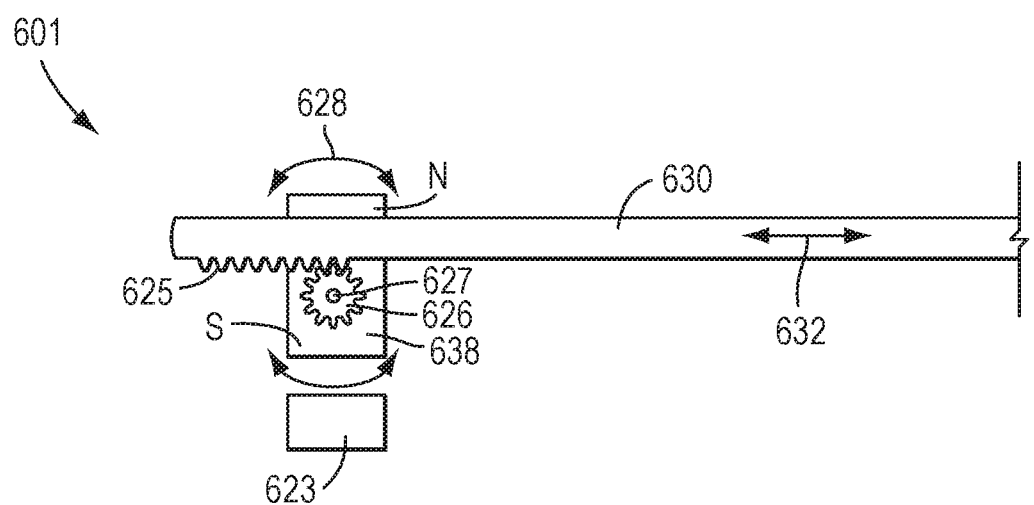
FIG. 6 is a schematic view of a portion of a cannula and a portion of a surgical instrument manipulator according to an exemplary embodiment.

For example, with reference now to FIG. 6, a schematic view of another exemplary embodiment of a portion of a return electrode sensing system 601 is shown. In the embodiment of FIG. 6, a pushrod 630 is connected to a magnet 638 by a rack 625 and pinion 626 gear set. The magnet 638 is rotatably attached (e.g., by a bearing, pin, etc.) to a cannula (e.g., at an attachment portion such as attachment portion 118 of cannula 100 (FIG. 2)) and positioned proximate a sensor 623 when the attachment portion 118 is engaged with the portion of the manipulator arm 122 (FIG. 2). The pushrod 630 moves along direction 632 as a return electrode connector (e.g., the return electrode connector 111 in FIG. 2) is engaged with, or disengaged from, a return electrode connector interface (e.g., the return electrode connector interface 110 in FIG. 3). Linear movement of the pushrod 630 is converted to rotational movement of the magnet 638 through the rack 625 and pinion 626 gear set. In other words, as the pushrod 630 moves along direction 632, the pinion gear 626 and magnet 638 rotate together about a rotational axis 627 of the pinion gear 626, as indicated by directional arrows 628. In the exemplary embodiment of FIG. 6, the magnet 638 has a north pole N and a south pole S. In the position illustrated in FIG. 6, the south pole S of the magnet 638 is positioned proximate the sensor 623 when the return electrode connector 111 is engaged with the return electrode connector interface 110. When the return electrode connector 111 is disengaged from the return electrode connector interface 110, movement of the pushrod 630 and the rack 625 causes the pinion 626 and magnet 638 to rotate 180 degrees, positioning the north pole N of the magnet 638 proximate the sensor 623. Information regarding which pole of the magnet 638 is positioned proximate the sensor 623 may be processed by the surgical system, and the surgical system user interface may provide a warning or lockout condition based on the connected or disconnected status of the return electrode connector 111.

While the above description is made with reference to a single magnet 338, any number or combinations of magnets of the array of magnets 336 may be configured to indicate the connected or disconnected state of the return electrode connector 112.

Figure 7:
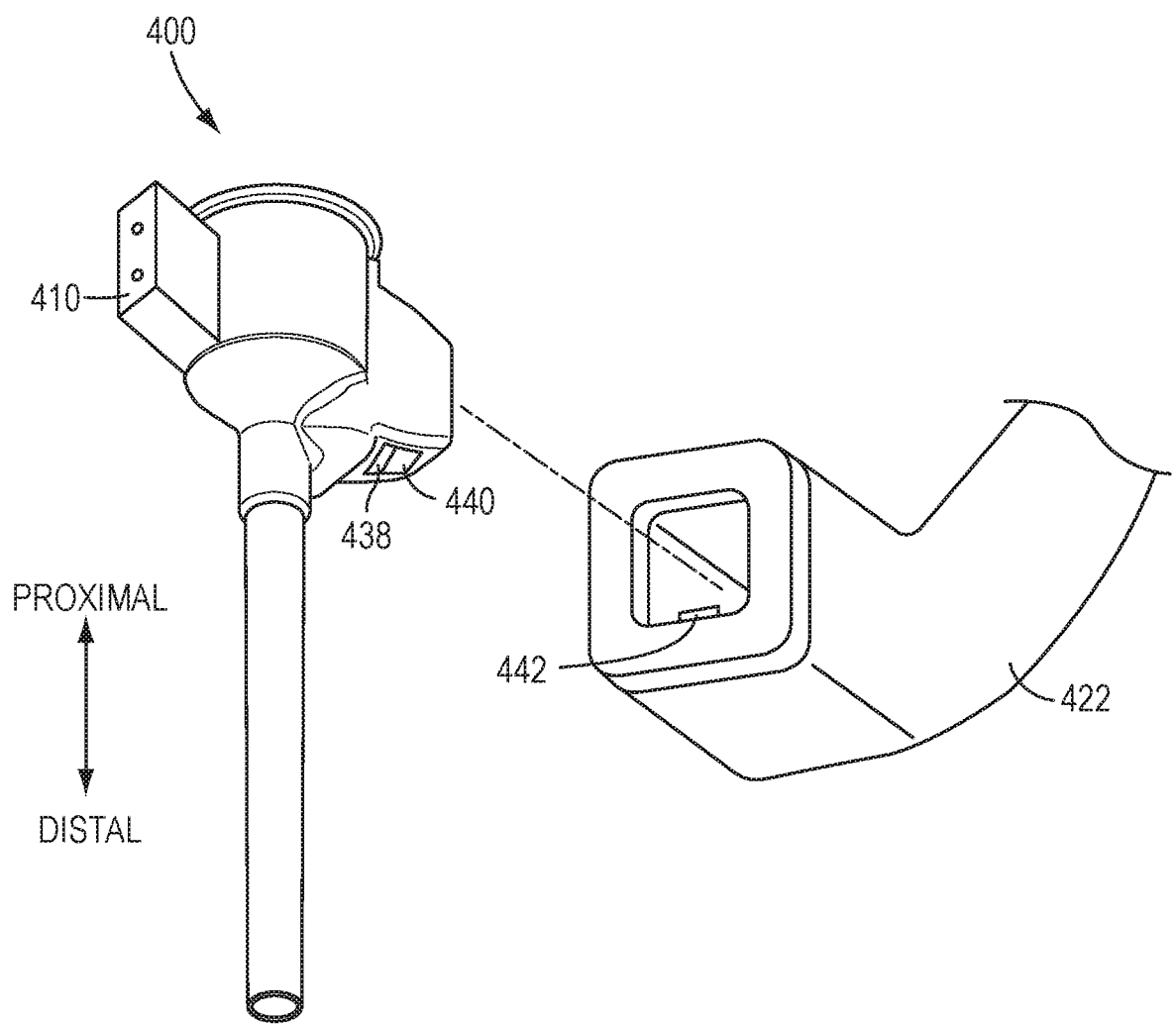
FIG. 7 is a perspective view of a cannula and a portion of a surgical instrument manipulator according to another exemplary embodiment.

In another exemplary embodiment, the connected or disconnected state of a return electrode connector (e.g., return electrode connector 112 shown in FIG. 3) with a cannula may be indicated by a proximity sensor. For example, FIG. 7 illustrates another exemplary embodiment of a surgical cannula 400 according to the disclosure. The surgical cannula 400 may have similar parts as surgical cannula 200 described in connection with FIGS. 3 through 4. However, the surgical cannula 400 includes a shutter 438 positioned in an opening 440 of an attachment portion 418 of the cannula 400. The shutter 438 is configured to move between a first position, in which the shutter 438 is outside of sensing proximity of a proximity sensor 442 disposed in a manipulator arm 422, and a second position, in which the shutter 438 is within sensing proximity of the proximity sensor 442. The proximity sensor 442 may comprise, for example, one or more of an optical proximity sensor, an electromagnetic proximity sensor, etc.

Movement of the shutter 438 between the first position and the second position may be caused by mating of a return electrode connector (e.g., return electrode connector 112 shown in FIG. 3) with a return electrode connector interface. For example, in the exemplary embodiment of FIG. 7, the cannula 400 includes a return electrode connector interface 410 similar to the interface 110 described above in connection with FIG. 2. In an exemplary embodiment, movement of the shutter 438 may be effected by a mechanism similar to the pushrod 230 described in connection with FIG. 3. Information regarding the connected or disconnected state of the return electrode connector may thus be provided in a manner otherwise similar to that discussed above in connection with the embodiment of FIGS. 2 through 4.

Although not illustrated in FIG. 5, the cannula 400 may also include an array of magnets similar to the array of magnets 336 described in connection with FIG. 4. Such an array may be similarly configured to provide information regarding various parameters of the cannula 400 to a surgical system of which the manipulator arm 422 forms a part as described above in connection with FIG. 4. However, those of ordinary skill in the art will appreciate that use of such a magnet array is optional.

Figure 8:
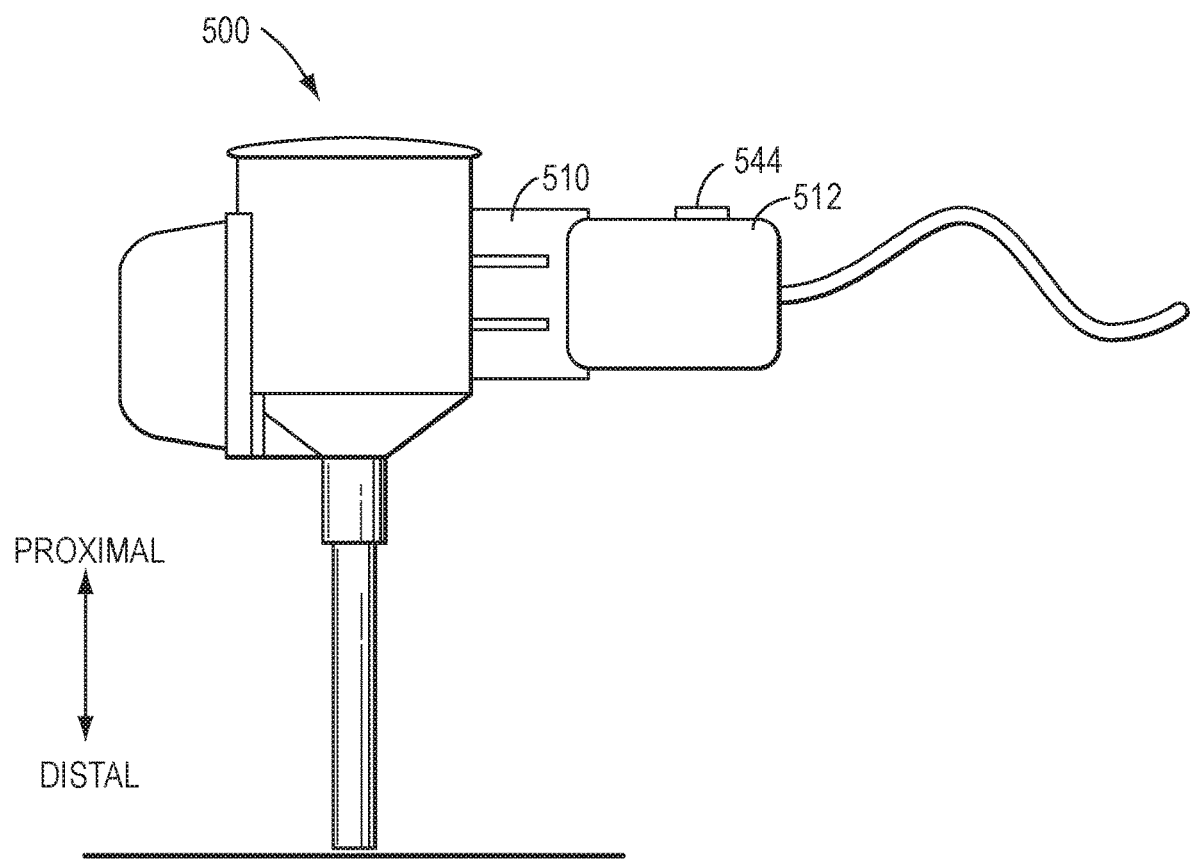
FIG. 8 side diagrammatic view of a cannula and a patient return electrode connector according to another exemplary embodiment.

Referring now to FIG. 8, another exemplary embodiment of a cannula 500 and a return electrode connector 512 according to the disclosure is shown. In this embodiment, the return electrode connector 512 includes a radio frequency identification (RFID) tag 544 configured and positioned to be recognized by an RFID sensor (not shown) positioned on a manipulator (e.g., manipulator 122 shown in FIG. 2) when the return electrode connector 512 is within a specified range of the RFID sensor. For example, the RFID tag 544 of the return electrode connector 512 is within the specified range of the RFID sensor when the return electrode connector 512 is engaged with a return electrode connector interface 510, and the RFID tag 544 is outside of the specified range of the RFID sensor when the return electrode connector 512 is disconnected from mating engagement with the return electrode connector interface 510, such as being removed from mating engagement with the return electrode connector interface 510. Thus, when the return electrode connector 512 is not in an electrically connected state with the cannula 500, the RFID sensor within the manipulator may recognize the absence of the RFID tag 544 of the return electrode connector 512. As described above, the surgical system may provide a visual or audible indication, or a lockout condition, based on the disconnected state of the return electrode connector 512.

In the exemplary embodiments of FIGS. 2, 3, 7, and 8, the electrical connector interface 110, 210, 410, and 510 is configured as a receptacle (i.e., female connector portion), and the connector 111, 112, and 512 is a plug (i.e., male connector portion) configured for insertion within the receptacle. However, as discussed above, those having ordinary skill in the art would appreciate that such an arrangement is exemplary in nature. For example, in some exemplary embodiments, the connector interface 110, 210, 410, and 510 may be configured as a plug and the electrical connector 111, 112, and 512 may be configured as a receptacle. Other exemplary embodiments may include different configurations of plugs and receptacles, or any other configuration of components configured to form an electrical and/or mechanical connection as described above.

Figure 9:
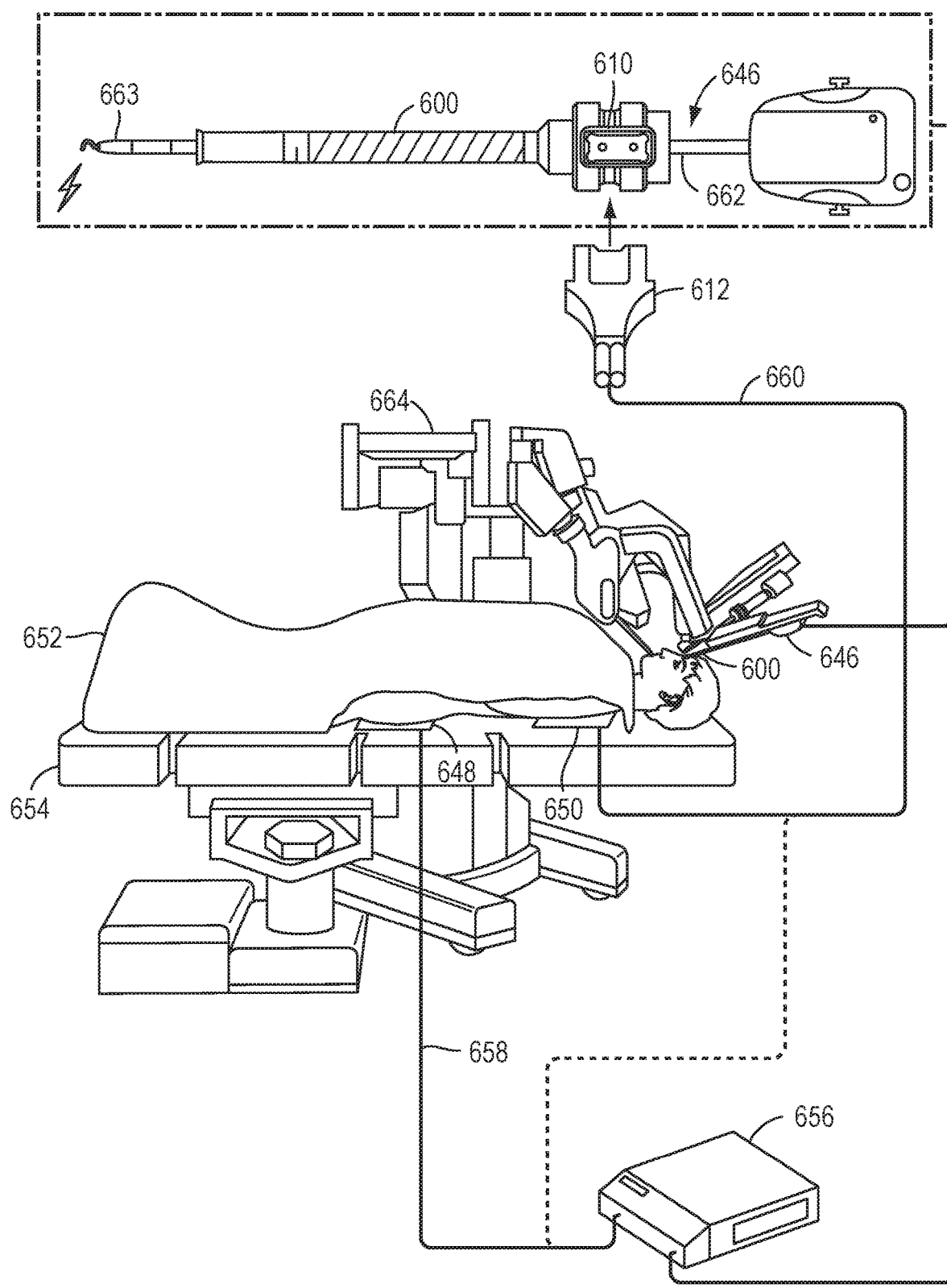
FIG. 9 is a diagrammatic view of a portion of a teleoperated surgical system according to an exemplary embodiment.

FIG. 9 is a diagrammatic view of an exemplary teleoperated surgical system, with a cannula 600 and an instrument 646 shown in place on a surgical system 664 as well as in detail view. The cannula 600 illustrated in FIG. 9 can be any one of cannulas 100, 200, 400, or 500, illustrated in FIGS. 2 through 4, 7 and 8. Return electrodes 648 and 650 are disposed beneath a patient 652 positioned on an operating table 654, for example, beneath the patient's shoulders and buttocks, or at other locations that provide sufficient surface area contact between the return electrodes 648 and 650 and the patient's body so as to permit electrical conductance therebetween. The return electrode 648 also is electrically coupled to an electrosurgical generator unit 656 through a cable 658. The electrode 650 is configured to be electrically coupled to the cannula 600 through a return electrode connector 612 of a cable 660 configured to connect with a return electrode connector interface 610 of the cannula 600. Such connection forms an electrical contact between the patient 652 and the cannula 600. An electrically conductive path is thus created from the cannula 600 to the patient 652 through the electrode 650, and to the electrosurgical generator unit 656 from the electrode 648.

The cannula 600 is configured to be disposed within an incision or orifice of the patient 652, such as within a surgical port (not shown). The instrument 646 may include a shaft 662 extending through the cannula 600 with an end effector 663 configured to perform a function such as, for example, stapling, cutting, cauterizing, suturing, clamping, etc., or combinations thereof. The cannula 600 and instrument 646 may be connected to a patient side manipulator 664, such as those disclosed at least in Intl Pub. No. WO2015/0142812, U.S. Patent App. Pub. No. US 2013/0325033, U.S. Patent App. Pub. No. US 2013/0325031, and U.S. Pat. No. 8,852,208, each of which is incorporated by reference above.

The cannula 600 and the patient side manipulator 664 may include a return electrode connection sensing system according to any of the exemplary embodiments described above in connection with FIGS. 2 through 8. For example, a return electrode connection sensing system may be configured to sense the engaged or disengaged state of the return electrode connector 612 with the return electrode connector interface 610 of the cannula 600, as described in the exemplary embodiments above.

The patient side manipulator 664 may be configured to provide various safety notifications and/or interlocks based on the engaged or disengaged state of the return electrode connector 612 with the return electrode connector interface 610 of the cannula 600. For example, as described above, a user interface (not shown) associated with the patient side manipulator 664 may be configured to provide a visual and/or audible notification to alert a user of the engaged or disengaged state of the return electrode connector interface 610 with the cannula 600. Additionally or alternatively, the user interface and/or the patient side manipulator may be configured to prevent application of electrical energy to the end effector 663 when the return electrode connector 612 is disengaged from the return electrode connector interface 610 of the cannula 600.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A surgical cannula, comprising:
    a bowl portion comprising an opening to permit removable insertion of a medical instrument into the bowl portion;
    a tube portion extending distally from the bowl portion and configured to removably receive and permit advancement of a medical instrument inserted through the bowl portion;
    an electrical connector interface at the bowl portion and configured to removably engage with an electrical connector electrically coupled to a patient return electrode, a state of engagement of the electrical connector interface being either an engaged state, in which the electrical connector interface is engaged with the electrical connector, or a disengaged state, in which the electrical connector interface is removed from engagement with the electrical connector; and
    an electrical connector sensing device configured to sense whether the electrical connector interface is in the engaged state or in the disengaged state,
    wherein the electrical connector sensing device is coupled to the bowl portion and is movable relative to the bowl portion between a first physical configuration and a second physical configuration;
    the electrical connector sensing device is in the first physical configuration in the engaged state of the electrical connector interface; and
    the electrical connector sensing device is in the second physical configuration in the disengaged state of the electrical connector interface.

2. The surgical cannula of claim 1, wherein the electrical connector sensing device comprises at least one magnet.

3. The surgical cannula of claim 2, wherein:
    the at least one magnet is coupled to the bowl portion of the surgical cannula and is movable relative to the bowl portion between a first position and a second position;
    the at least one magnet is in the first position in the first physical configuration of the electrical connector sensing device; and
    the at least one magnet is in the second position in the second physical configuration of the electrical connector sensing device.

4. The surgical cannula of claim 2, wherein:
    the at least one magnet is coupled to the bowl portion of the surgical cannula and is movable relative to the bowl portion between a first rotational orientation and a second rotational orientation;
    the at least one magnet is in the first rotational orientation in the first physical configuration of the electrical connector sensing device; and
    the at least one magnet is in the second rotational orientation in the second physical configuration of the electrical connector sensing device.

5. The surgical cannula of claim 1, wherein the electrical connector sensing device comprises a pushrod coupled to the bowl portion of the surgical cannula and configured to move relative to the bowl portion from a first position corresponding to the first physical configuration of the electrical connector sensing device to a second position corresponding to the second physical configuration of the electrical connector sensing device.

6. The surgical cannula of claim 5, wherein the pushrod is in mechanical contact with the electrical connector in the engaged state of the electrical connector interface.

7. The surgical cannula of claim 6, wherein:
    the electrical connector interface comprises a receptacle; and
    a portion of the pushrod is disposed within the receptacle such that the electrical connector contacts the pushrod as the electrical connector is inserted into the receptacle, and the electrical connector is configured to exert a force via the contact with the pushrod sufficient to move the pushrod from the first position to the second position.

8. The surgical cannula of claim 5, wherein:
    the electrical connector sensing device comprises a magnet coupled to the bowl portion and movable relative to the bowl portion between a first position and a second position; and
    movement of the pushrod between the first and second positions of the pushrod causes the magnet to move between the first and second positions of the magnet.

9. The surgical cannula of claim 1, wherein:
    the electrical connector sensing device is not electrically powered.

10. The surgical cannula of claim 1, wherein:
    the electrical connector sensing device comprises a shutter configured to move between a first position and a second position;
    the shutter is in the first position in the first physical configuration of the electrical connector sensing device; and
    the shutter is in the second position in the second physical configuration of the electrical connector sensing device.

11. The surgical cannula of claim 1, wherein the electrical connector sensing device comprises a radio-frequency identification device.

12. The surgical cannula of claim 1, further comprising an attachment portion protruding laterally from a sidewall of the bowl portion and configured to be removably coupled with a portion of a manipulator arm of a surgical system.

13. The surgical cannula of claim 12, wherein:
    the attachment portion includes an array of magnets configured to communicate identification information regarding the surgical cannula to a sensor at the manipulator arm; and
    the electrical connector sensing device is further configured to use a magnet of the array of magnets to output a signal indicative of the state of the electrical connector interface.

14. The surgical cannula of claim 1, wherein the electrical connector sensing device is further configured to output a signal containing information regarding the engaged or disengaged state of the electrical connector interface.

15. A surgical system, comprising:
    a surgical manipulator;
    a cannula configured to be removably mounted to the surgical manipulator, the cannula comprising:
        a bowl portion comprising an opening to permit removable insertion of a medical instrument into the bowl portion while the cannula is in a mounted state,
        a tube portion extending distally from the bowl portion and configured to removably receive and permit advancement of a medical instrument inserted through the bowl portion, and
        an electrical connector interface at the bowl portion and configured to removably engage with an electrical connector electrically coupled with a patient return electrode, a state of engagement of the electrical connector interface being either an engaged state, in which the electrical connector interface is engaged with the electrical connector, or a disengaged state, in which the electrical connector interface is removed from engagement with the electrical connector;

an electrical connector sensing device arranged to sense the state of engagement of the electrical connector interface; and a controller operably coupled to the electrical connector sensing device, the controller receiving information from the electrical connector sensing device regarding the state of engagement of the electrical connector interface with the electrical connector, wherein the electrical connector sensing device is coupled to the bowl portion and is movable relative to the bowl portion between a first physical configuration and a second physical configuration;

the electrical connector sensing device is in the first physical configuration in the engaged state of the electrical connector interface; and the electrical connector sensing device is in the second physical configuration in the disengaged state of the electrical connector interface.

16. The surgical system of claim 15, further comprising a user interface configured to display a visible notification of the disengaged state of the electrical connector interface.

17. The surgical system of claim 15, wherein the surgical system is configured to provide an audible notification of the disengaged state of the electrical connector interface.

18. The surgical system of claim 15, wherein at least one function of the surgical system is configured to be disabled based on the patient return electrode being electrically decoupled from the electrical connector interface.

19. The surgical system of claim 15, wherein:

the electrical connector sensing device comprises a magnet coupled to the bowl portion of the cannula and movable relative to the bowl portion between a first position and a second position;

the magnet is in the first position in the first physical configuration of the electrical connector sensing device;

the magnet is in the second position in the first physical configuration of the electrical connector sensing device;

the electrical connector sensing device further comprises a magnetic reader at the surgical manipulator; and the magnetic reader is configured to sense the magnet and generate a signal indicating the engaged state of the electrical connector interface with the electrical connector based on sensing the magnet in the first position.

* * * * *